(12) United States Patent
DeCerce

(10) Patent No.: US 12,383,414 B2
(45) Date of Patent: Aug. 12, 2025

(54) ORTHOPEDIC MEASUREMENT SYSTEM

(71) Applicant: HOWMEDICA OSTEONICS CORP., Mahwa, NJ (US)

(72) Inventor: Joseph DeCerce, Fort Lauderdale, FL (US)

(73) Assignee: HOWMEDICA OSTEONICS CORP., Mahwa, NJ (US)

( * ) Notice: Subject to any disclaimer, the term of this patent is extended or adjusted under 35 U.S.C. 154(b) by 367 days.

(21) Appl. No.: 17/663,191

(22) Filed: May 12, 2022

(65) Prior Publication Data

US 2022/0362037 A1    Nov. 17, 2022

Related U.S. Application Data

(60) Provisional application No. 63/188,296, filed on May 13, 2021.

(51) Int. Cl.
| | | |
|---|---|---|
| *A61F 2/46* | (2006.01) | |
| *G16H 20/40* | (2018.01) | |
| *G16H 40/63* | (2018.01) | |

(52) U.S. Cl.
CPC ........... *A61F 2/4657* (2013.01); *G16H 20/40* (2018.01); *G16H 40/63* (2018.01); *A61F 2002/4666* (2013.01)

(58) Field of Classification Search
CPC ........................ A61F 2/4657; A61F 2002/4666
See application file for complete search history.

(56) References Cited

U.S. PATENT DOCUMENTS

| | | | |
|---|---|---|---|
| 7,381,223 | B2 | 6/2008 | Kovacevic |
| 7,412,897 | B2 | 8/2008 | Crottet et al. |
| 8,494,805 | B2 | 7/2013 | Roche et al. |
| 8,689,647 | B2 | 4/2014 | Stein |
| 9,265,462 | B2 | 2/2016 | McIntosh et al. |
| 10,531,826 | B2 | 1/2020 | Wasielewski et al. |
| 2009/0005708 | A1 | 1/2009 | Johanson et al. |
| 2012/0179069 | A1 | 7/2012 | Amirouche |
| 2019/0076273 | A1* | 3/2019 | Goodchild ........... A61B 5/6878 |
| 2020/0107943 | A1* | 4/2020 | Trousdale ............. A61B 34/25 |

FOREIGN PATENT DOCUMENTS

CN       103957790 B    1/2017

\* cited by examiner

*Primary Examiner* — Si Ming Ku
(74) *Attorney, Agent, or Firm* — Bookoff McAndrews, PLLC

(57) ABSTRACT

A measurement system comprising a measurement device and a computer. The measurement device is configured to measure a force, pressure, or load applied by the musculoskeletal system. The measurement device comprises an enclosure and a structure configured to fit within an opening in the enclosure. The enclosure is hermetically sealed housing electronic circuitry and at least one sensor. The structure is configured to couple to the musculoskeletal system. At least three sensors underlie and couple to the structure to measure a force, pressure, or load applied to a surface of the structure. The structure includes at least three anti-cantilevering structures. At least one of the three anti-cantilevering structures is configured to couple to the enclosure to limit canting of the structure when the musculoskeletal system couples to the surface of the structure outside a predetermined area.

18 Claims, 6 Drawing Sheets

ORTHOPEDIC MEASUREMENT SYSTEM

CROSS-REFERENCE TO RELATED APPLICATIONS

This application claims the benefit of priority under 35 U.S.C. § 119 from U.S. Provisional Application No. 63/188,296, filed on May 13, 2021, which is incorporated by reference herein in its entirety.

FIELD

The present disclosure relates generally to orthopedic medical devices, and more specifically to devices that generate quantitative measurement data in real-time.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, prosthetic orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance. It would be of great benefit if quantitative measurement data could be provided in real-time to support a subjective feel of a surgeon in an operating room environment for the installation of one or more prosthetic components.

DETAILED DESCRIPTION

Figure 1:
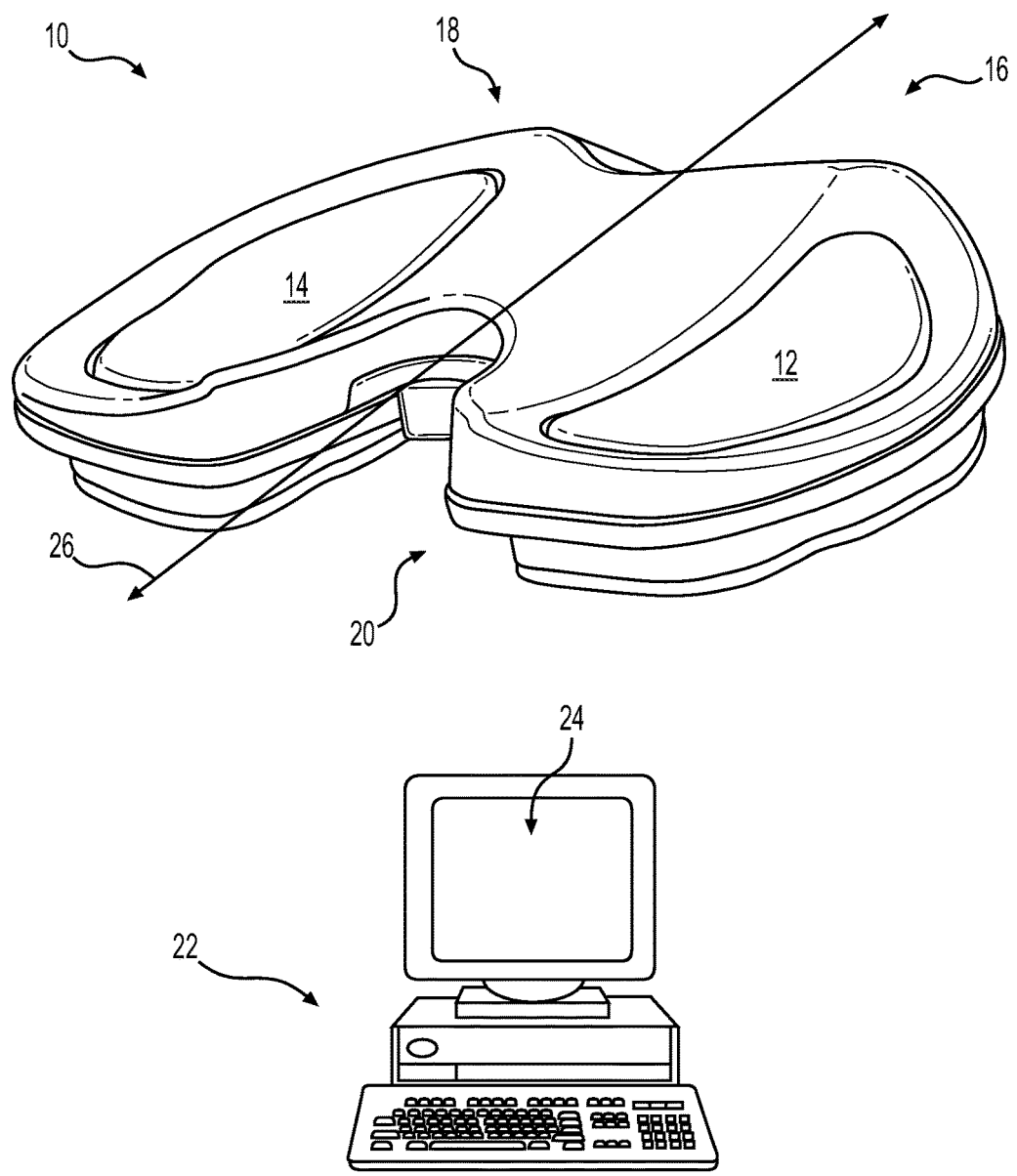
FIG. 1 is an illustration of a measurement system configured to couple to a musculoskeletal system in accordance with an example embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the measurement apparatus are illustrative only and do not limit use for other parts of a body. In general, the measurement system disclosed herein can be used to measure parameters of the musculoskeletal system. The measurement system or the measurement device can also support installation of prosthetic components to the musculoskeletal system. The measurement system can be coupled to a bone, knee, hip, ankle, spine, shoulder, hand, wrist, foot, fingers, toes, and other areas of the musculoskeletal system to measure at least one parameter. In one embodiment, the measurement system is configured to measure parameters that support a calculation of a position of applied load by the musculoskeletal system and the load magnitude at the position of applied load. The measurement system supports measurement of parameters in real-time during surgery to provide information to a surgeon or surgical team. In general, the principles disclosed herein are meant to be adapted for use in orthopedic pre-operative planning, intra-operative assessment, post-operative assessment, rehabilitation, and long-term monitoring of the musculoskeletal system. In one embodiment, the measurement system is configured to be within a joint of the musculoskeletal system and support movement of the joint. In one embodiment, the measurement system can have a similar shape or form factor as a prosthetic component that is subsequently coupled to the musculoskeletal system.

The following description of embodiment(s) is merely illustrative in nature and is in no way intended to limit the invention, its application, or uses. For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

Processes, techniques, apparatus, and materials as known by one of ordinary skill in the art may not be discussed in detail but are intended to be part of the enabling description where appropriate. In all of the examples illustrated and discussed herein, any specific materials, temperatures, times, energies etc. . . . for process steps or specific structure implementations should be interpreted to be illustrative only and non-limiting. Processes, techniques, apparatus, and materials as known by one of ordinary skill in the art may not be discussed in detail but are intended to be part of an enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device. The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging, IMU (inertial measurement unit), accelerometer, magnetometer, gyroscope, inclinometers, or MEMs devices) can be used within the scope of the embodiments described. The tracking devices can be used to determine position, trajectory, movement, or motion in real-time. The tracking devices can also support measurement of joint rotation and joint alignment.

At least one embodiment is directed to a kinetic orthopedic measurement system to aid a surgeon in determining real time alignment, range of motion, loading, impingement, and contact point of orthopedic implants. Although the system is generic to any orthopedic surgery (e.g., spinal, shoulder, knee, hip, ankle, wrist, finger, toe, bone, musculoskeletal, etc.) the following example(s) deal with orthopedic surgery as a non-limiting example of an embodiment of the invention.

The non-limiting embodiment described herein is related to quantitative measurement based orthopedic surgery and referred to herein as the kinetic system. The kinetic system includes a sensor system that provides quantitative measurement data and feedback that can be provided visually, audibly, or haptically to a surgeon or surgical team. The kinetic system provides the surgeon real-time dynamic data regarding force, pressure, or loading on the joint, contact and congruency through a full range of motion, and information regarding impingement.

In general, kinetics is the study of the effect of forces upon the motion of a body or system of bodies. Disclosed herein is a system for kinetic assessment of the musculoskeletal system. The kinetic system can be for the installation of prosthetic components or for monitoring and assessment of permanently installed components to the musculoskeletal system. For example, installation of a prosthetic component can require one or more bone surfaces to be prepared to receive a device or component. The kinetic system is designed to take quantitative measurements of at least the load, position of load, or alignment with the forces being applied to the joint similar to that of a final joint installation. The sensored measurement components are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled.

A prosthetic joint installation can benefit from quantitative measurement data in conjunction with subjective feedback of the prosthetic joint to the surgeon. The quantitative measurements can be used to determine adjustments to bone, prosthetic components, or tissue prior to final installation. Permanent sensors can also be housed in final prosthetic components to provide periodic data related to the status of the implant. Data collected intra-operatively and long term can be used to determine parameter ranges for surgical installation and to improve future prosthetic components. The physical parameter or parameters of interest can include, but are not limited to, measurement of height, length, width, tilt/slope, position, orientation, load magnitude, force, pressure, contact point location, displacement, density, viscosity, pH, light, color, sound, optical, vascular flow, visual recognition, humidity, alignment, position, rotation, inertial sensing, turbidity, bone density, fluid viscosity, strain, angular deformity, vibration, torque, elasticity, motion, acceleration, infection, pain, or temperature. Often, several measured parameters are used to make a quantitative assessment. A graphical user interface can support assimilation of measurement data in real-time during surgery. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

At least one embodiment is directed to a system for adjusting or monitoring a contact position of a musculoskeletal joint for stability comprising: a tool, device, or prosthetic component configured to rotate after being coupled to a bone; a tool, device, or sensored prosthesis having an articular surface to support movement of the musculoskeletal system, where the tool, device, or sensored prosthesis has a plurality of sensors coupled to a surface and a position tracking system configured to measure position, slope, rotation, or trajectory in 3D space, and a computer system configured to wirelessly receive quantitative measurement data from the tool, device, or sensored prosthesis where the computer includes a display to provide the measurement data to a surgical team, a doctor, medical staff, or patient. In one embodiment, the computer system and display is within the operating room where the surgical procedure is performed.

In the present invention parameters are measured with an integrated wireless sensing module or device comprising an encapsulating structure that supports sensors and contacting surfaces and an electronic assemblage that integrates a power supply, one or more sensors, one or more pressure sensors, transducers, one or more inertial sensors, antennas and electronic circuitry that processes measurement data as well as controlling operation of energy conversion, detection, measurement, and wireless communications. The wireless sensing module or device can be positioned on or within, or engaged with, or attached or affixed to or within, a wide range of physical systems including, but not limited to instruments, appliances, vehicles, equipment, or other physical systems as well as animal and human bodies, for sensing and communicating parameters of interest in real time.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

In one embodiment, a patient can receive quantitative measurement data from one or more sensors coupled to the musculoskeletal system, installed prosthetic component or coupled to bone. Thus, the patient can be monitored pre-operatively for assessment, intra-operatively to support installation of a prosthetic component or repair of the musculoskeletal system, and post-operatively after being released from surgery and during rehabilitation using the sensor technology. The measurement data can support optimization of therapy and indicate problems that may occur. The effects of the therapy program using the intelligent prosthetic components can be linked to proper joint function and the patient can be educated on the recovery relative to their specific plan and supported by clinical evidence from a prosthetic component data base. In one embodiment, when the prosthesis is activated, the data will be transmitted (RF/Bluetooth) to a patient recovery application. In one embodiment, the application can be on a computer or a device such as a smart phone. The quantitative measurement data from the sensors will be uploaded into a cloud based VPN (virtual private network) that is HIPPA Compliant. The quantitative measurement data can be assessed by one or more computer programs and updates, work flows, and the measurement data can be sent to the treating physician and health care team. The intelligent prosthesis can be used to support post-op exercises, treatment, or pharmaceuticals that can accelerate the healing phase. Furthermore, different reconstruction techniques can be compared with real-time data. Evaluations of the effects of reconstruction when combined with multi ligamentous injuries can also be analyzed. Healing phase monitoring related to graft adherence to the host tunnels (bone to bone, tendon to bone, composite to bone) can provide quantitative measurement data related thereto. Other important parameters can also be generated such as improving range of motion ROM and terminal extension, achieving improved muscle strength, improved proprioception, improved stability, and improved gait mechanics.

FIG. 1 is an illustration of a measurement system 10 configured to couple to a musculoskeletal system in accordance with an example embodiment. Measurement system 10 comprises one or more sensors configured to measure one or more parameters, a computer 22, and a display 24. Electronic circuitry couples to the one or more sensors to control a measurement process and transmit measurement data. In one embodiment, the electronic circuitry and the one or more sensors are hermetically sealed within measurement system 10. Measurement system 10 can adapted for use pre-operatively, intra-operatively, or post-operatively to generate measurement data. Measurement data from measurement system 10 is configured to be transmitted to computer 22. In one embodiment, computer 22 and display 24 include one or more computer programs to process the measurement data, a graphical user to provide the measurement data, provide one or more actions based on the measurement data, generate workflows, or convert the measurement data into a form that can be rapidly assimilated by users of measurement system 10. In one embodiment, measurement system 10 is configured to be used intra-operatively during surgery to support installation of one or more prosthetic components. The quantitative measurement data from measurement system 10 is configured is used to optimize installation of one or more prosthetic components. Similarly, measurement system 10 can be part of one or more prosthetic components installed in the musculoskeletal system. The measurement data from measurement system 10 in a prosthetic component can provide information related to infection detection, pain mitigation, alignment, wear, range of motion, rotation, position, glue joint integrity, or other longer term maintenance issues that can affect reliability or performance of the joint or prosthetic component. Measurement system 10 provides measurement data in real-time that is processed by computer 22 and displayed on display 24.

In the example, measurement system 10 is used intra-operatively to support an installation of a prosthetic component. Measurement system 10 comprises an upper housing 18 and a lower housing 20 that couple together to form enclosure 16. In one embodiment, enclosure 16 is hermetically sealed to seal electronic circuitry and sensors within enclosure 16 from an external environment. A structure 12 and a structure 14 couple respectively within a first opening and a second opening in upper housing 18. Structure 12 and structure 14 are configured to move relative to the enclosure 16. In the example, enclosure 16 couples within a joint of the musculoskeletal system. In one embodiment, measurement system 10 is configured to couple within a knee joint. Condyles of a femur respectively couple to structures 12 and 14. A tibia is configured to couple to lower housing 20. Measurement system 10 is configured to support movement of the knee joint while generating measurement data. In one embodiment, measurement system 10 measures loading at predetermined locations on a surface of structure 12 and at predetermined locations on a surface of structure 14. In one embodiment, the predetermined locations on the surface of structure 12 are vertexes of a polygon. Similarly, the predetermined locations on the surface of structure 14 are vertexes of a polygon. In one embodiment, the polygon of structure 12 can be different in size or shape from the polygon of structure 14. In one embodiment, a sensor underlies each predetermined location of structures 12 and 14. A force, pressure, or load is applied to structure 12 and structure 14 by the musculoskeletal system. Structures 12 and 14 can move relative to enclosure 16 such that the force, pressure, or load is applied to the sensors underlying structure 12 or structure 14.

Computer 22 receives measurement data from measurement system 10. In one embodiment, computer 12 calculates a position of applied load to structure 12 or structure 14. The position of applied load can also be called a contact point where the condyles of the femur couple to structure 12 or structure 14. Computer 22 calculates the position of applied load using the predetermined locations on the surface of structure 12 or structure 14 and the load magnitude at the predetermined locations on the surface of structure 12 or structure 14. Computer 22 also calculates the load magnitude at the position of applied load on structure 12 or structure 14 from the measurement data. In one embodiment, the position of applied load and the load magnitude at the position of applied load is displayed on display 24 of computer 22 in real-time. In one embodiment, a change in loading on a sensor underlying structure 12 or structure 14 will result in a change in the position of applied load and the load magnitude at the position of applied load. The surface of structure 12 is above a surface of enclosure 16 adjacent to the surface of structure 12. Similarly, the surface of structure 14 is above a surface of enclosure 16 adjacent to the surface of structure 12. In general, the position of applied load is designed to be applied only to structure 12 or structure 14. In one embodiment, the position of applied load moving off structure 12 or structure 14 is considered an error that needs to be corrected and will be indicated on display 24 of computer 22. In one embodiment, the surgical team is notified by computer 22 when the position of applied load moves to an adjacent area of enclosure 16 and leaves structure 12 or structure 14. Note that the sensors underlying structure 12 or structure 14 will change from being loaded to unloaded if a condyle of the femur moves from being on structure 12 or structure 14 to the surface that is adjacent on enclosure 16. Alternatively, the surface of structure 12 or the surface of structure 14 can be contoured such that the surface is not planar. The surface can have a contour that prevents or limits movement to decouple from the surface of structure 12 or structure 14 as the point of applied load moves toward the edge of structure 12 or structure 14. In any case, display 24 will show movement of the point of applied load and the movement of the point of applied load over a range of motion of the joint. Further discussion herein below of the operation of measurement system 10 may describe a single side showing operation of structure 12 or structure 14. It should be noted that operation of structure 12 and structure 14 on either side of double arrow 26 will operate similar so what is disclosed herein below will correspond to operation of structure 12 and structure 14 and the disclosed material applies to either structure of measurement system 10.

Figure 2A:
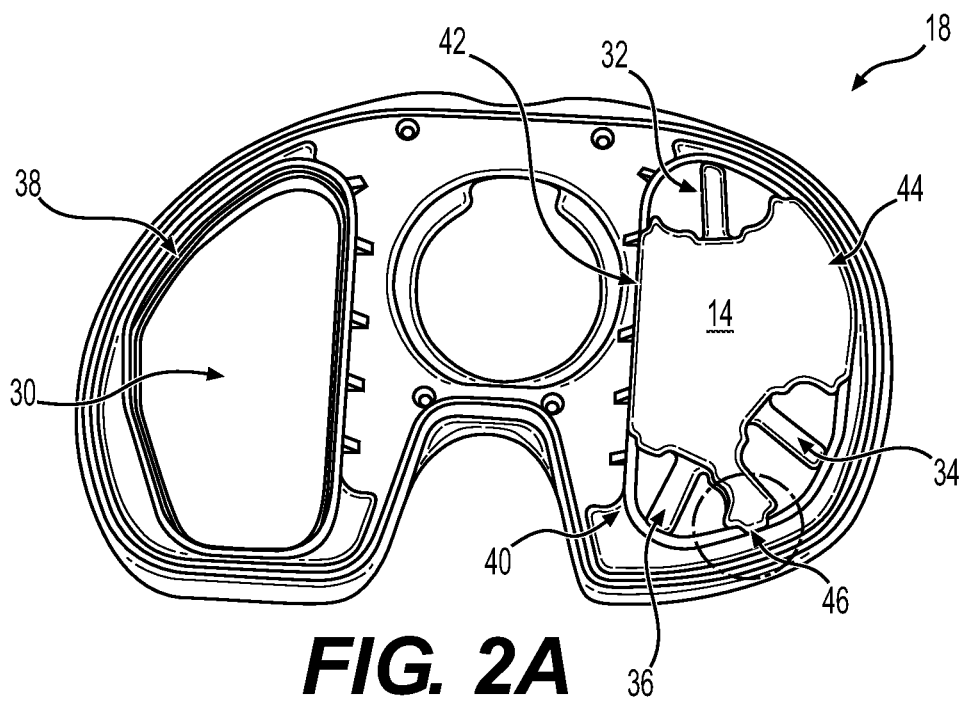
FIG. 2A is an illustration of an upper housing illustrating an opening in accordance with an example embodiment.

FIG. 2A is an illustration of upper housing 18 illustrating an opening 30 in accordance with an example embodiment. An interior view of upper housing 18 has structure 12 of FIG. 1 removed with structure 14 coupled to upper housing 18. A periphery 38 is a region of upper housing 18 that is adjacent to opening 30. Similarly, a periphery 40 of upper housing 18 is adjacent to an opening of upper housing 18 in which structure 14 is placed within. In the example, three sensors will underlie structure 12 of FIG. 1 and three sensors will underlie structure 14. In the example, a first sensor will underlie and couple to area 32 of structure 14, a second sensor will underlie and couple to an area 34 of structure 14, and a third sensor will underlie and couple to an area 36 of structure 14. In one embodiment, area 32, area 34, and area 36 couple to vertexes of a polygon on the surface of structure 14. The polygon in the example is a triangle. The vertexes of the polygon on the surface of structure 14 related to area 32, 34, and 36 are known by computer 22 of FIG. 1. The musculoskeletal system will couple to the surface structure 14 at a position of applied load or contact point. The position of applied load is calculated by computer 22 of FIG. 1 using the measurement data from the first, second, and third sensors and the position of the vertexes on the surface of structure 14. Computer 22 of FIG. 1 can further calculate the load magnitude at the position of applied load using the load magnitudes measured at the vertexes of the polygon. The position of applied load and the load magnitude applied to structure 12 and 14 are calculated in real-time and displayed on display 24. The load magnitude and the position of applied load will move as the loading changes at the vertexes of the polygon. An anti-cantilever structure 42, an anti-cantilever structure 44, and an anti-cantilever structure 46 are formed on structure 14. In one embodiment, anti-cantilever structures 42, 44, and 46 over hang periphery 40 of upper housing 18. The anti-cantilever structures 42, 44, and 46 are configured to limit cantilevering or to prevent canting of structure 14 to support measurement of the position of applied load and load magnitude at the position of applied load when the position of applied load is outside the polygon. Structure 12 will also have similar anti-cantilever structures. In general, there will be at least three anti-cantilever structures on structure 12 or structure 14 to limit cantilevering of structure 12 or structure 14 when the position of applied load is outside the polygon. At least one of the three anti-cantilever structures will prevent canting of structure 12 or 14 as the position of applied load to the surface of structure 12 or 14 approaches the outermost regions outside the polygon.

Figure 2B:
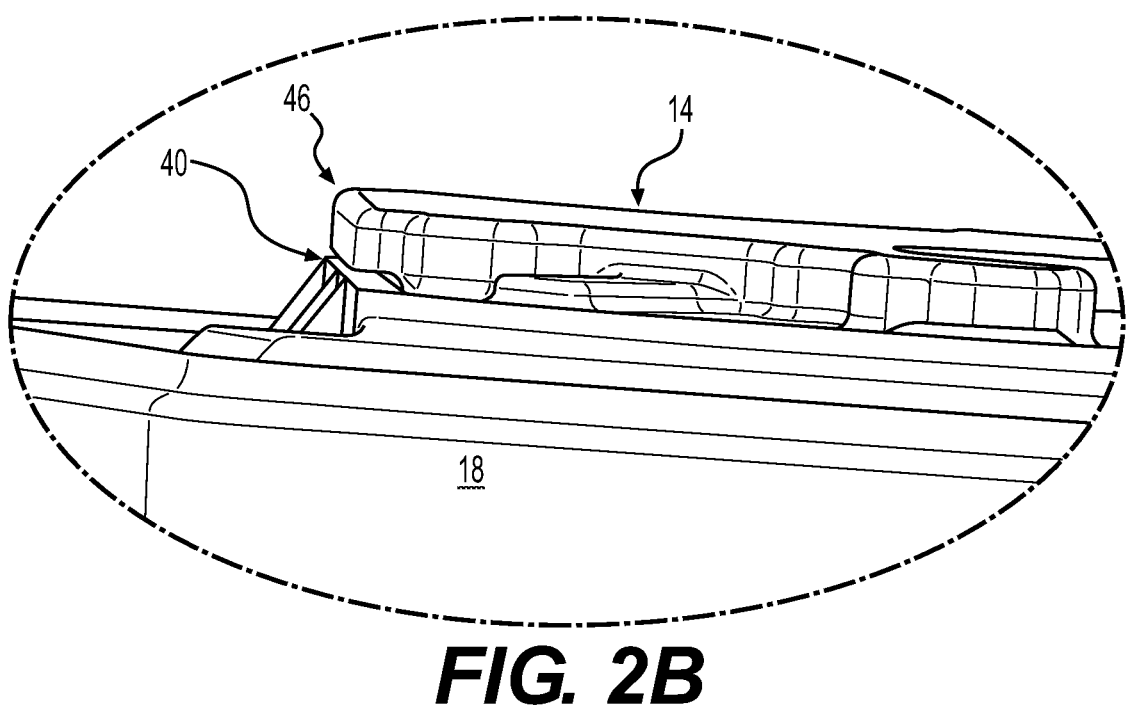
FIG. 2B is a magnified view of an anti-cantilever structure over hanging a periphery of the upper housing in accordance with an example embodiment.

FIG. 2B is a magnified view of anti-cantilever structure 46 over hanging periphery 40 of upper housing 18 in accordance with an example embodiment. The view is an interior view of upper housing 18 showing structure 14 within the opening in upper housing 18. Anti-cantilever structures 42 and 44 of FIG. 2 overhang periphery 40 of upper housing 18 similarly. In one embodiment, anti-cantilever structure 46 is spaced a predetermined distance between a surface of periphery 40 of upper housing 18 and anti-cantilever structure 46 when the surface of structure 14 is unloaded. Similarly, anti-cantilever structures 42 and 44 are spaced from periphery 40 of upper housing 18 by the same predetermined distance when the surface of structure 14 is unloaded. Anti-cantilever structure 46 limits cantilevering of structure 14 when the position of applied load is outside the polygon in an area that moves anti-cantilever structure 46 towards periphery 40 of upper housing. In general, the musculoskeletal system applying a force or load to an area on the surface of structure 14 on the opposite side from where anti-cantilever structure 46 is located will cause structure to cantilever. Further movement towards the edge of the surface of structure 14 will cause anti-cantilever structure 46 to couple to periphery 40. Structure 14 is prevented from further cantilevering when anti-cantilever structure 46 couples to periphery 40 of upper housing 18. Anti-cantilever structure 42 and 44 operates similarly to prevent cantilevering when the position of applied load is outside the polygon in areas that cause either anti-cantilever structure 42 or 44 to cantilever and couple to periphery 40 of upper housing 18. Anti-cantilever structures 42, 44, and 46 of FIG. 2 limits unloading of one or more sensors when the position of applied load is outside the vertexes of the polygon. Moreover, anti-cantilever structures 42, 44, and 46 of FIG. 2 allow the position of applied load and the load magnitude at the position of applied load to the surface of structure 14 to be measured accurately as the position of applied load moves outside the polygon.

Figure 3:
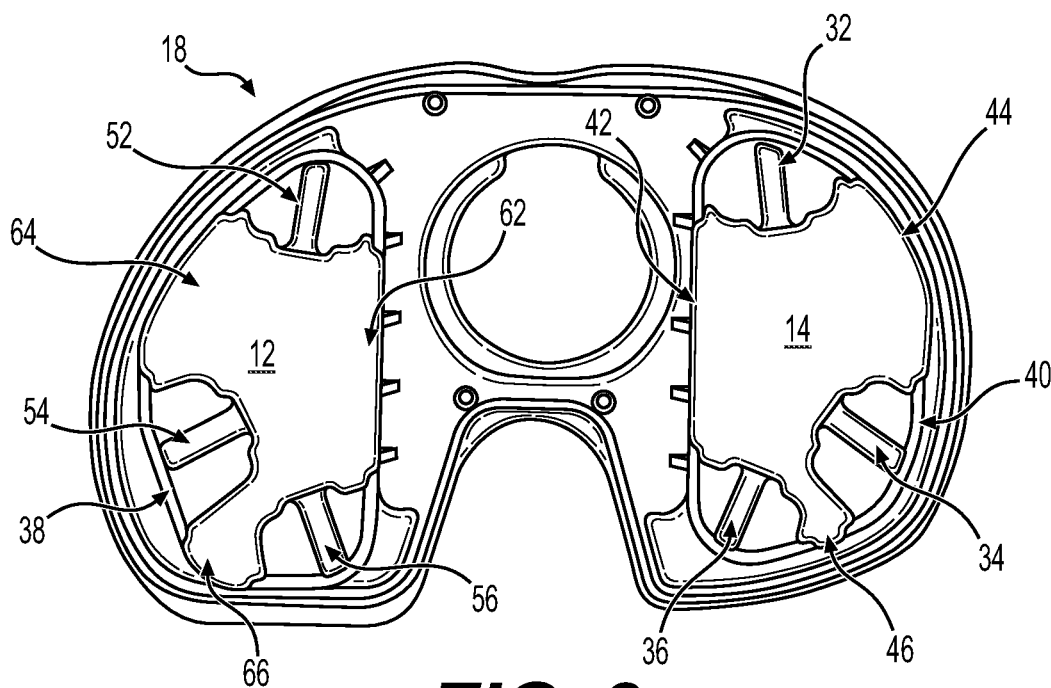
FIG. 3 is an illustration of the interior of the upper housing with structures within openings in accordance with an example embodiment.
Figure 4:
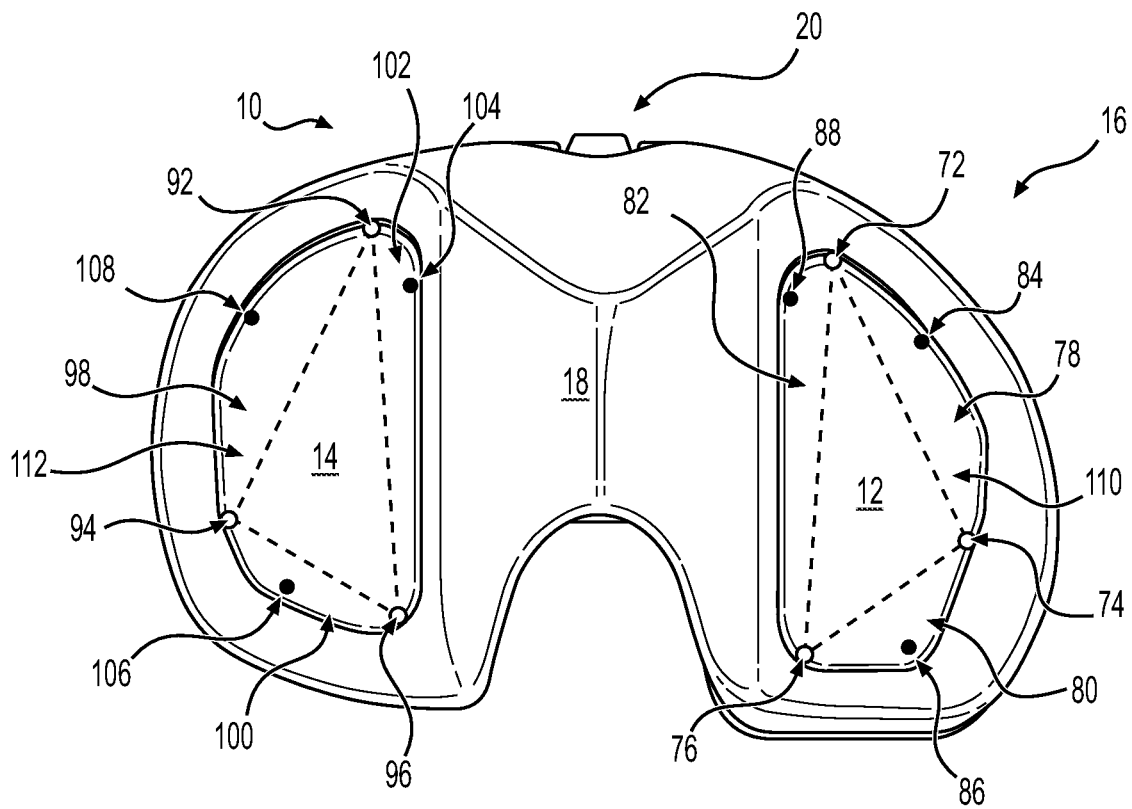
FIG. 4 is an illustration of the surfaces of the structures in accordance with an example embodiment.

FIG. 3 is an illustration of the interior of upper housing 18 with structure 12 and structure 14 within openings in accordance with an example embodiment. More specifically, structure 12 is coupled within opening 30 shown in FIG. 2A. Upper housing 18 has periphery 38 adjacent to opening 30 of FIG. 2. In one embodiment, area 52, area 54, and area 56 couple to vertexes of a polygon on the surface of structure 12. The vertexes of the polygon on the surface of structure 14 related to area 52, 54, and 56 are known by computer 22 of FIG. 1. Area 52, area 54, and area 56 each couple to a sensor configured to measure loading such as a capacitor, strain gauge, MEMs device, piezo device or other sensors configured to measure a parameter related to measuring a force, pressure, or load. In the example, the polygon of structure 12 is a triangle with three corresponding sensors configured for measuring the force, pressure, or load applied by the musculoskeletal system to the surface of structure 12. Structure 12 also has anti-cantilevering structures to limit cantilevering or canting of structure 12 when the position of applied load to the surface of structure 12 is outside the polygon. In general, structure 12 and structure 14 has at least three anti-cantilevering structures to limit canting of structure 12 or structure 14. Anti-cantilevering structures 62, 64, and 66 are shown underlying periphery 38 adjacent to the opening in which structure 12 fits in upper housing 18. Anti-cantilevering structures 62, 64, and 66 support measurement of the loading when the position of applied load is outside the polygon. Anti-cantilevering structures 62, 64, and 66 are spaced a predetermined distance from periphery 38 of upper housing 18. A load applied outside the polygon will cause structure 12 to cant. In one embodiment, canting occurs on an opposing side from which the load is applied. The cant of structure 12 will increase as the position of applied load moves away from the boundary of the polygon until one or more of anti-cantilevering structures 62, 64, or 66 couple to periphery 38 of upper housing 16. Thus, structure 12 is allowed to cant the predetermined distance before being stopped from any further canting even if the position of applied load moves farther from the boundary of the polygon. Referring briefly to FIGS. 3 and 4, anti-cantilevering structures 42, 44, and 46 operate similarly for structure 14 as discussed herein above for coupling to periphery 40 of upper housing 18 as structure 14 cants due to the position of applied load moving outside the boundary of triangle 110

FIG. 4 is an illustration of the surfaces of structure 12 and structure 14 in accordance with an example embodiment. A triangle 110 and a triangle 112 are respectively drawn on structure 12 and structure 14. Triangle 110 has vertexes 72, 74, and 76 that couple to sensors respectively underlying areas 52, 54, and 56. Triangle 112 has vertexes 92, 94, and 96 that couple to sensors underlying areas 32, 34, and 36. In one embodiment, triangles 110 and 112 can differ in area, size, and shape. In general, accurate measurement of the position of applied load and the load magnitude at the position of applied load on the surface of structures 12 and 14 can be calculated when the position of applied load is at the boundary or within triangles 110 and 112. The loading is distributed to each sensor underlying each vertex when the position of applied load is in or at the boundary of triangle 110 or triangle 112. Thus, each sensor is operating within a normal load range that is configured to provide accurate measurement of a portion of the total force, pressure, or load magnitude applied at the position of applied load. As previously, mentioned the measurement data is transmitted to computer 22 of FIG. 1 and the force, pressure, or load measurement data measured at the vertexes of triangle 110 or triangle 112 is used to calculate the position of applied load on within triangles 110 or 112 and the load magnitude at the position of applied load. Computer 22 of FIG. 1 also has the location of the vertexes of triangle 110 or 112 to support the calculation of the position of applied load and the load magnitude at the position of applied load.

Measurement of the position of applied load and the load magnitude at the position of applied load is less accurate outside of the boundary of the polygon. In general, a force, pressure, or load applied to the surface of structure 12 or structure 14 outside triangle 110 or triangle 112 can produce canting of structure 12 or structure 14. Canting occurs because the surface of structure 12 or structure 14 is loaded outside one or more vertexes. Note that structures 12 or 14 couple loading applied to the surface to a sensor underlying each vertex. Thus, the position of applied load being applied outside the triangle 112 or triangle 114 causes one or more sensors to become a pivot point as they are interior to the position of applied load thereby causing structure 12 or structure 14 to cant. In one embodiment, the error is minimized or corrected by computer 22 of FIG. 1 to produce the position of applied load and the load magnitude at the position of applied load with an error that is acceptable for the application. How this is done will be disclosed in more detail here in below. Also, one or more sensors at the vertexes of the polygon may become lightly loaded or unloaded as the position of applied load moves outside the boundary of the polygon. Measurement data from the lightly loaded or unloaded sensors may be outside a measurement range of a sensor for tracking the position of applied load or be less accurate. Conversely, all or most of the loading can be placed on a single sensor at the vertex of the polygon when the loading is outside the boundary of the polygon. Measurement data from the heavily loaded sensor may be outside the measurement range of a sensor for tracking the position of applied load or be less accurate. In one embodiment, a surgeon or surgical team have a need to track the position of applied load and the load magnitude at the position of applied load when the position of applied load moves outside the boundary of the polygon. Measurement system 10 is configured to support accurate measurement outside the polygon.

In the example, the polygons of measurement system 10 are triangles 110 and 112. A sensor couples to and underlies each vertex 72, 74, and 76 of triangle 110 on the surface of structure 12. Similarly, a sensor couples to and underlies each vertex 92, 94, and 96 of triangle 112 on the surface of structure 14. In one embodiment, vertexes 72, 74, and 76 of triangle 110 and vertexes 92, 94, and 96 of triangle 110 are placed at or near a periphery of structure 12 or structure 14. In the example, a region 78, a region 80, and a region 82 are defined as regions outside of triangle 110. Referring briefly to FIG. 3, anti-cantilevering structures 42, 44, and 46 of structure 14 and anti-cantilevering structures 62, 64, and 66 of structure 12 are configured to respectively limit canting of structures 14 and 12 and support accurate measurement outside of triangle 110 and triangle 112. The point of applied load coupling to the farthest distance from the boundary of triangle 12 or triangle 14 will have the worst error. In general, regions 78, 80, and 82 on the surface of structure 12 or regions 98, 100, and 102 on the surface of structure 14 have different shapes such that the farthest distance from the boundary will differ for each region. In the example, the locations farthest from the boundary of triangle 110 on the surface of structure 12 is location 84 in region 78, location 86 in region 80, and location 88 in region 82. The locations farthest from the boundary of triangle 112 on the surface of structure 14 are location 104, location 106, and location 108. The maximum measurement error would occur at locations 84, 86, or 88 or locations 104, 206, and 108.

Figure 5:
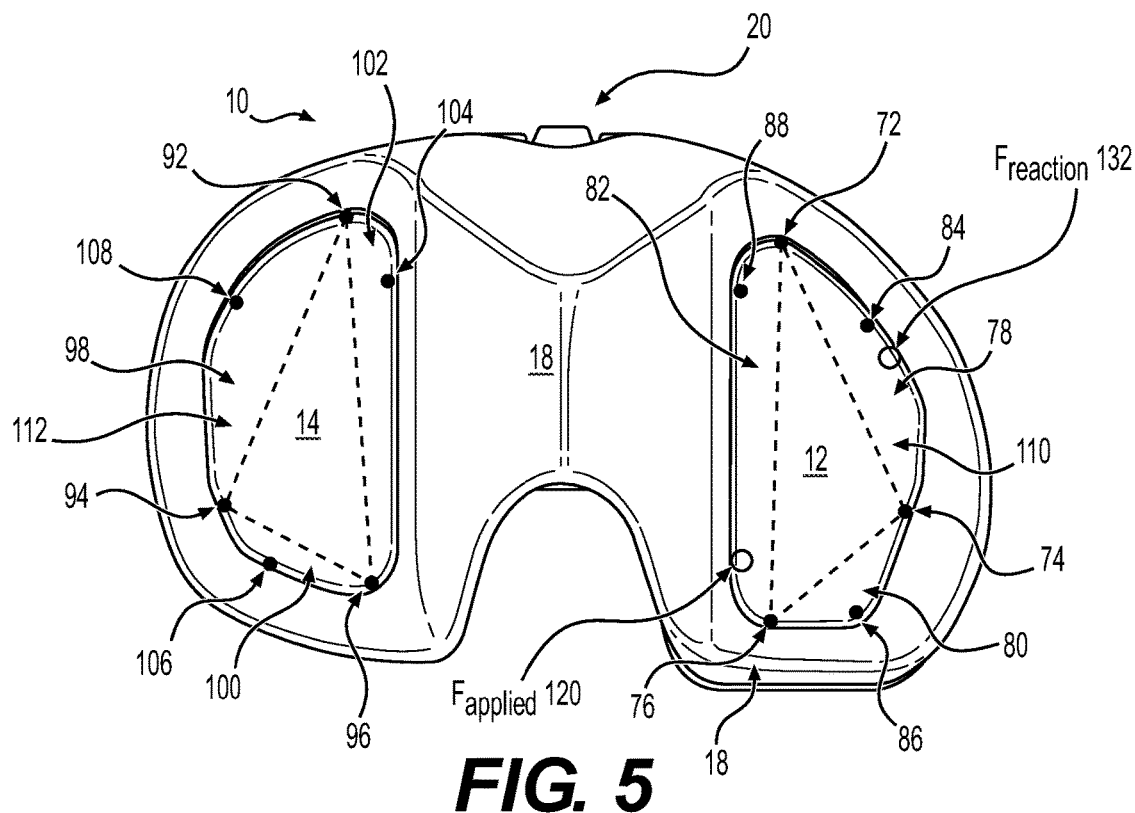
FIG. 5 is top view of the measurement system with loading of the musculoskeletal system applied to the surface of the structure outside the triangle in accordance with an example embodiment.

FIG. 5 is top view of measurement system 10 with loading of the musculoskeletal system applied to the surface of structure 12 outside triangle 110 in accordance with an example embodiment. Measurement system 10 supports load measurement when the load is applied within triangle 110 and as the position of applied load moves outside triangle 110. In one embodiment, measurement system 10 is used in surgery to provide measurement data to support installation of a prosthetic component. In the example, measurement system 10 is used to support the installation of a knee joint. The condyles of a femur are configured to couple to structures 12 and 14. The position of applied load on structure 12 and structure 14 is a contact point where a condyle of the femur couples to structure 12 or structure 14. In one embodiment, the contact point of the medial or lateral condyle of the femur does not remain stationary on the surface of structure 12 or the surface of structure 14 as the leg is moved through a range of motion. In one embodiment, the position of applied load moving outside triangle 110 or triangle 112 is considered acceptable over the range of motion. In other words, the position of applied load and the load magnitude at the position of applied load on the surface of structure 12 or structure 14 is tracked and reported by computer 22 and displayed on display 24 for measurement system 10.

An example of loading outside triangle 110 is disclosed to illustrate what occurs in measurement system 10 to provide accurate position of applied load and the load magnitude at the position of applied load as the position of applied load transitions from within triangle 110 to moving outside triangle 110. Although the example is directed toward structure 12 the operation of structure 14 will operate similarly. Also, the disclosed concept relates to the position of applied load moving outside triangle 110 or 112 respectively in regions 78, 80, and 82 or regions 98, 100, and 102. In general, the process disclosed herein below can be used to measure the position of applied load and the load magnitude in regions outside the boundary of any polygon shape and is not limited to a triangle in the example. In the example, $F_{applied}$ 120 is applied in region 82 of the surface of structure 12 outside of triangle 110. $F_{applied}$ 120 is in proximity to vertex 76 of triangle 110. As mentioned previously, a sensor underlies vertex 76 for providing measurement data at vertex 76 to support calculation of the position of applied load. $F_{applied}$ 120 being applied outside triangle 110 in region 82 causes structure 12 to cant. In the example, an anti-cantilevering structure will limit canting of structure 12 and produce a $F_{reaction}$ 132 counteracting force outside region 78. In general, canting movement of structure 12 is prevented by anti-cantilevering structures 62, 64, or 66 coupling to upper housing 18 of FIG. 6. More than one of anti-cantilevering structures 62, 64, or 66 can couple to upper housing 18 as structure 12 to prevent canting.

Figure 6:
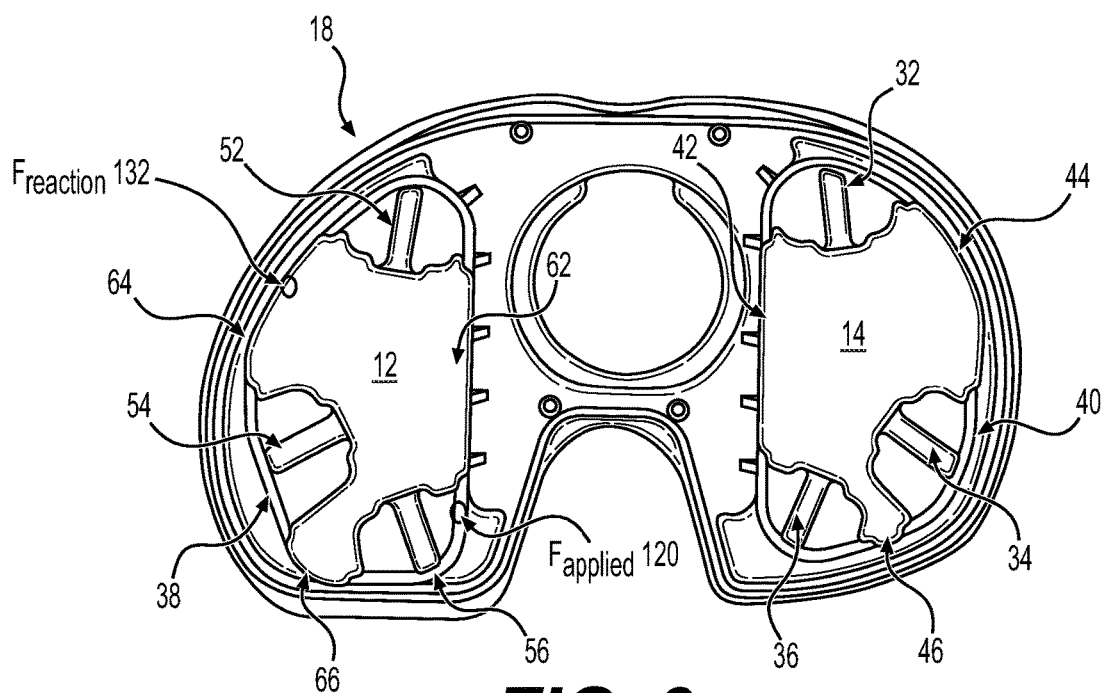
FIG. 6 is an illustration showing an interior view of the upper housing with the structures in accordance with an example embodiment.

FIG. 6 is an illustration showing an interior view of upper housing 18 with structures 12 and 14 in accordance with an example embodiment. Areas 52, 54, and 56 on an interior surface of structure 12 respectively couple to vertexes 72, 74, and 76 on the surface of structure 12 of FIG. 5. A first, second, and third sensor respectively underlies each area 52, 54, and 56. A position of applied load on the surface of structure 12 distributes the force, pressure, or load to the first, second, and third sensors through areas 52, 54, and 56 on the interior surface of structure 12. Similarly, areas 32, 34, and 36 on an interior surface of structure 14 respectively couple to vertexes 92, 94, and 96 on the surface structure 14. A fourth, fifth, and sixth sensor respectively underlies each area 32, 34, and 36. A position of applied load on the surface of structure 14 distributes the force, pressure, or load to the first, second, and third sensors through areas 32, 34, and 36.

Anti-cantilevering structures 62, 64, and 66 overlie a portion of periphery 38 of structure 12 adjacent to the opening in which structure 12 is fitted. Similarly, anti-cantilevering structures 42, 44, and 46 of structure 14 overlie a portion of periphery 40 adjacent to the opening in which structure 14 is fitted. In general, a position applied load in a region outside the boundary of the polygon will cause the load bearing structure to cant upward on an opposing side to the position of applied load. One or more anti-cantilevering structures will limit or prevent canting thereby applying an opposing force, pressure, or load to prevent further canting. The spacing between anti-cantilevering structures 62, 64, and 66 and upper housing 18 when no canting is occurring is a minimum spacing defined by tolerances in manufacturing and assembly of measurement system 10 to ensure a gap. In one embodiment, the spacing between anti-cantilevering structures 62, 64, and 66 and periphery 38 of upper housing 18 is 0.254 millimeters when the position of applied load is within the boundary of triangle 110. The spacing between anti-cantilevering structure 42, 44, and 46 of structure 14 and periphery 40 of structure 14 is also 0.254 millimeters when the position of applied load is within the boundary of triangle 112. In general, the point at which one or more anti-cantilevering structures 62, 64, and 66 will couple to periphery 38 can vary and is determined by the position of applied load as it moves outside the boundary of triangle 110. Referring briefly to FIG. 5, $F_{applied}$ 120 the position of applied load is shown outside the boundary of triangle 110. $F_{applied}$ 120 cants structure 12 such that anti-cantilevering structure 64 of structure 12 couples to periphery 38 of structure 12. In the example, anti-cantilevering structure 64 produces $F_{reaction}$ 132 in an area shown in FIG. 5 that prevents further canting. $F_{reaction}$ 132 is shown on the interior view of structure 12 that couples anti-cantilevering structure 64 to periphery 38 of structure 12. In one embodiment, the entire anti-cantilevering structure 64 can be coupled to periphery 38 of structure 12 or a portion of anti-cantilevering structure 64 can be coupled to periphery 38 of structure 12 depending on the position applied load which causes structure 12 to cant. As mentioned previously, more than one anti-cantilevering structure can couple to periphery 38 of structure 12. $F_{reaction}$ 132 is then divided between the one or more anti-cantilevering structures coupling to periphery 138 to generate a force that opposes canting of structure 12.

Figure 7:
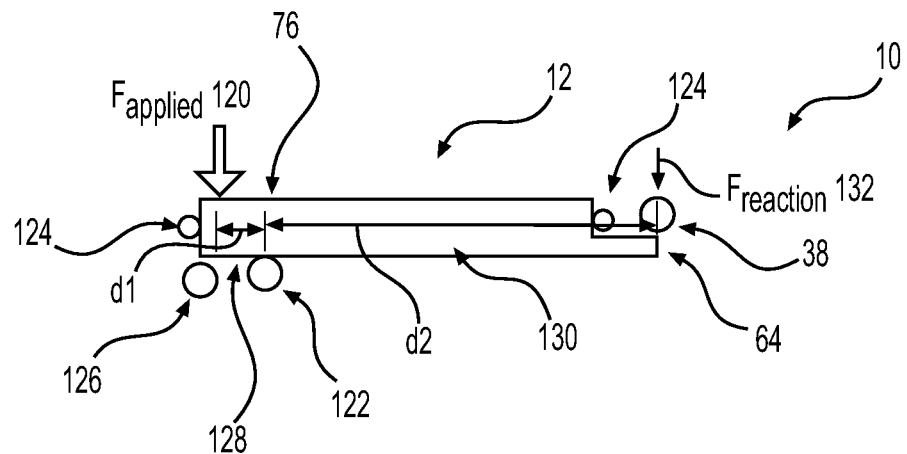
FIG. 7 is an illustration of a force being applied outside the boundary of the polygon in accordance with an example embodiment.

FIG. 7 is an illustration of a force being applied outside the boundary of the polygon in accordance with an example embodiment. A simplified view of a structure shows what occurs when a force is applied outside the boundary of the polygon on the surface of the structure in a measurement system. In the example, the polygon on the surface of structure 12 is triangle 110 as shown in FIG. 5 having vertexes 72, 74, and 76. A first sensor, a second sensor, and a third sensor respectively underlie vertexes 72, 74, and 76 and are configured to measure a force, pressure, or load at each location. A computer 22 shown in FIG. 1 is configured to receive measurement data and calculate the position of applied load and the load magnitude at the position of applied load using the force, pressure, or load measurement data and the locations of vertexes 72, 74, and 76. As mentioned previously, inaccuracies in measurement can occur when the position of applied load moves outside the boundary of triangle 110. The inaccuracy will increase as the position of applied load moves farther from the boundary of triangle 110.

Enclosure 16 of FIG. 1 is hermetically sealed from an external environment. Upper housing 18 is coupled to lower housing 20 to form enclosure 16 in FIG. 1. In one embodiment, upper housing 18 and lower housing 20 are coupled together by an adhesive. Structures 12 and 14 of FIG. 1 have a seal to isolate an interior of enclosure 16 from an external environment while allowing structures 12 and 14 to move relative to enclosure 16. Movement of structures 12 and 14 relative to enclosure 16 support measurement of the position of applied load and the load magnitude at the position of applied load. Structure 12 of FIG. 7 is sealed to upper housing 18 of FIG. 5 by an O-ring 124. O-ring 124 comprises a compressible and flexible material such as silicone that couples around structure 12 or structure 14. O-ring 124 couples between a sidewall in the opening of upper housing 18 of FIG. 2A and a sidewall of structure 12. The spacing between the sidewall of upper housing 18 and the sidewall of structure 12 is less than the thickness of O-ring 124 to ensure O-ring 124 compresses to form a compression seal. O-ring 124 supports movement of structure 12 relative to enclosure 16 of FIG. 1 when a force, pressure, or load is applied to the surface of structure 12. Enclosure 16 of FIG. 1 further includes a stop 126 as shown in FIG. 7 that is configured to protect sensor 122. Sensor 122 underlies vertex 76 of FIG. 5. In the example, stop 126 prevents movement of structure 12 prior to $F_{applied}$ 120 being at a level that can damage sensor 122. Conversely, stop 126 does not couple to structure 12 when $F_{applied}$ 120 is being applied to the surface of structure 12 that is in a normal operating range of sensor 122. Stop 126 stops movement of structure 12 such that the loading to sensor 122 cannot be increased after a predetermined spacing is exceeded between structure 12 and stop 126. In one embodiment, the predetermined spacing between structure 12 and stop 126 is 0.508 millimeters which is sufficient to protect sensor 122 from being damaged when a load is applied to structure 12 above the allowed maximum loading. In one embodiment, the stop 126 is coupled to lower housing 20 of FIG. 1. In one embodiment, a plurality of stops are formed in lower housing 20 of FIG. 1 to protect each sensor coupled to structure 12 and each sensor coupled to structure 14 from over-excursion damage.

Referring to FIG. 5, the position of applied load to the surface of structure 12 is applied to region 82 near vertex 76. $F_{applied}$ 120 is a force, pressure, or load applied to the surface of structure 12 outside the boundary of triangle 110 of FIG. 5. Although a specific example is provided, any force, pressure, or load applied to the surface of structure 12 outside the boundary of triangle 110 of FIG. 5 will be calculated similarly. A sensor 122 as shown in FIG. 7 underlies vertex 76 and is configured to measure loading applied at vertex 76. Note that sensor 122 acts as a pivot point when $F_{applied}$ 120 is outside the boundary of triangle 110 of FIG. 5. Conversely, sensor 122 is not a pivot point that causes structure 12 to cant when $F_{applied}$ 120 is at the boundary or within the boundary of triangle 110 of FIG. 5. In the example, $F_{applied}$ 120 is applied a distance 128 corresponding to $d_1$ in FIG. 7 from vertex 76. A distance 132 corresponding to $d_2$ in FIG. 7 is a distance from vertex 128 to an opposing side of structure 112 having anti-cantilevering structure 64 of FIG. 6 overlying periphery 38 of structure 12. $F_{applied}$ 120 applied as indicated in FIG. 6 will cause structure 12 to cant towards upper housing 18 ultimately coupling anti-cantilevering structure 64 to periphery 38 of structure 12 of FIG. 6. As shown, in FIG. 7, anti-cantilevering structure 64 has not coupled to structure 12. $F_{reaction}$ 132 is a force applied by enclosure 16 and more specifically periphery 38 of upper housing 18 of FIG. 3 to prevent structure 12 from further canting. In general, an increase in $F_{applied}$ 120 will result in a corresponding increase in $F_{reaction}$ 132 applied by upper housing 18 to structure 12. As mentioned previously, the predetermined distance between anti-cantilevering structure 64 of structure 12 and periphery 38 of upper housing 18 is 0.254 millimeters that is supported by the manufacturing and assembling tolerances of enclosure 16 of FIG. 1.

Figure 8:
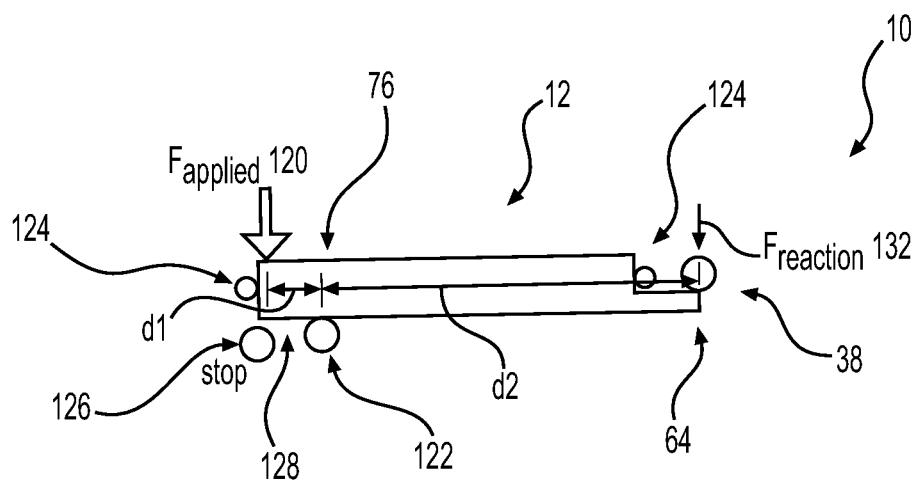
FIG. 8 is an illustration of the structure canting due to a force, pressure, or load being applied to the surface outside the triangle of FIG. 5 in accordance with an example embodiment.

FIG. 8 is an illustration of structure 12 canting due to a force, pressure, or load being applied to the surface outside triangle 110 of FIG. 5 in accordance with an example embodiment. In the example, the force, pressure, or load is applied to region 82 of FIG. 5 near vertex 76 causing structure 12 to cant. In the example, $F_{applied}$ 120 is applied to the location indicated in FIG. 5 causing structure 12 to cant and coupling anti-cantilevering structure 64 to periphery 38 of upper housing 18. More specifically, canting of structure 12 causes region 78 of FIG. 5 to lift or cant when loading is applied near vertex 76 in region 82. As shown in FIG. 6 canting of structure 12 and more specifically region 78 of FIG. 5 results in anti-cantilevering structure 64 coupling to periphery 38 of upper housing 18 thereby preventing further canting of structure 12. Structure 12 movement is limited by periphery 38 of upper housing 18 even if $F_{applied}$ 120 is increased. $F_{reaction}$ 132 is generated to oppose the canting of structure 12 corresponding to anti-cantilevering structure 64 of structure 12 coupling to periphery 38 of upper housing 18.

Measurement data from sensor 122 requires correction when $F_{applied}$ 120 is outside the boundary of triangle 110 in region 82 and periphery 38 of upper housing 18 of FIG. 3 couples to anti-cantilevering structure 64 of structure 12. A first equation (1) relates $F_{reaction}$ 132 to $F_{applied}$ 120 as shown herein below. A second equation (2) relates $F_{measured}$ to $F_{reaction}$ and $F_{applied}$ and is shown herein below for the example. Note that computer 22 of FIG. 1 will calculate the position of applied load and the load magnitude at the position of applied load from the measurement data generated by the sensors underlying each vertex of the polygon.

$$F_{reaction}132 = F_{applied}120 * d_1/d_2. \quad (1)$$

$$F_{measured} = F_{reaction}132 + F_{applied}120 \quad (2)$$

In one embodiment, $F_{measured}$ can be estimated without having measurement data for $F_{reaction}$ 132. The estimate used if the error is within a range that is acceptable for the surgeon or surgical team in monitoring the position of applied load and the load magnitude at the position of applied load over a range of motion. The worst error will occur at the farthest distance from a boundary in regions 78, 80, or 82 as shown in FIG. 5. The farthest points within regions 78, 80, or 82 from the boundary of triangle 110 are respectively identified as location 84, location 86, and location 88 of FIG. 5. In one embodiment, the error in measurement by measurement system 10 will be largest at locations 84, 86, and 88 of FIG. 5. We can solve for $F_{reaction}$ using equation (1) and then use the results in equation 2 to determine $F_{measured}$ as a ratio of the distances $d_1/d_2$. Equation (3) relates measurement error at location 84 to $F_{measured}$ that is actually measured by measurement system 10. Equation (4) relates measurement error at location 82 to $F_{measured}$ that is actually measured by measurement system 10. Equation (5) relates measurement error at location 86 to $F_{measured}$ that is actually measured by measurement system 10. Note that the error at the different locations within a region 78, 80, or 82 will vary because $d_1$ and $d_2$ differs in each region due to a difference in shape of each region. $D_1$ is the distance from a vertex to the position of applied load at locations 84, 86, and 88. $D_2$ is the distance from the vertex to the anti-cantilevering structure that couples to upper housing 18 of FIG. 6 when structure 12 is canted.

$$\text{Error at Location 84:} = d_1/d_2 * F_{measured} \quad (4)$$

$$\text{Error at Location 82:} = d_1/d_2 * F_{measured} \quad (5)$$

$$\text{Error at Location 86:} = d_1/d_2 * F_{measured} \quad (6)$$

In the example shown in FIG. 5 for structure 12, the maximum error ($\text{Max}_{error}$) at location 84, 82, and 86 is ($d_1/d_2$) 15% at location 84, ($d_1/d_2$) 13% at location 82, and ($d_1/d_2$) 7% at location 86. In one embodiment, the error is chosen as a constant for each region. In one embodiment, the error is chosen to be different for each region 78, 80, 82 of structure 12 and related to the maximum error at locations 84, 86, and 88. In one embodiment, the error selected for calculating the measured loading outside the boundary of triangle 110 is less than the maximum error. In the example disclosed herein above, the error is selected to be half of the maximum error ($0.5 * \text{Max}_{error}$) to calculate an approximate load magnitude when the position of applied load is outside the boundary of triangle 110 of FIG. 5. Computer 22 is used to calculate $F_{approximate}$ at the position of applied load as stated in equation (7).

$$F_{approximate} = F_{measured}(1 + \tfrac{1}{2}(\text{Max}_{error} \text{ for region})) \quad (7)$$

Thus, the correction increases the loading measured by measurement system 10 when the position of applied load is in regions 78, 80, or 82. One half of maximum error ($\text{Max}_{error}$) in regions, 78, 80, and 82 is respectively 7.5%, 3.5%, and 6.5%. Computer 22 determines the region in which the position of applied load is in and selects the appropriate $\text{Max}_{error}$ for the region. The $F_{measured}$ by measurement system 10 is used with equation (7) to calculate $F_{approximate}$ which is the calculated loading at the position of applied load. Note that $F_{approximate}$ is an estimated force. The error in the approximation of the load magnitude at the position of applied load in regions 78, 80, and 82 is respectively limited to an error less than or equal to 7.5%, 3.5%, or 6.5% of the $F_{measured}$ by measurement system 10. In one embodiment, this error is acceptable for applications to support installation of one or more prosthetic components in a joint of the musculoskeletal system.

In the example, computer 22 receiving measurement data from measurement system 10 would determine that the position of applied load is in region 82 of the surface of structure 12. Computer 22 uses 13.5% as the error correction as disclosed above for that region. Computer 22 would also calculate the load magnitude at the position of applied load which is $F_{applied}$ 120. Computer then outputs the approximate loading in region 82 as stated in equation (8) herein below. The measurement error using this calculation method would be less than or equal to 6.5% of $F_{approximate}$. Although disclosed for structure 12 of measurement system 10, the calculation method can be applied similarly for structure 14. Different polygons can be used to reduce the maximum error by reducing the distance outside the boundary of the polygon and the distance to a vertex. Computer 22 will have different maximum error ($\text{Max}_{error}$) for each region outside the boundary of a polygon. For the calculation, the measurement error is minimized by adding $0.5 * (\text{Max}_{error})$ to the measured force, pressure, or load as the position of applied load traverses outside the boundary of the polygon into any region. Each region can have a different ($\text{Max}_{error}$) due to geometrical differences as disclosed herein. As mentioned, this measurement methodology is supported with the minimum number of sensors and provides accuracy suitable for monitoring musculoskeletal loading over a range of motion. Typically, the majority of the position of applied load will be within the polygon measurement system 10 but computer 22 will provide $F_{approximate}$ measurement data in regions outside the polygon of structure 12 or structure 14. In one embodiment, a different multiplier other than 0.5 can be used to further reduce error if the typical paths outside the boundary of the polygon for the application does not extend to ($\text{Max}_{error}$) as calculated herein above. Knowledge of the range of motion paths for measurement system 10 can be incorporated to further reduce error in measurement.

$$F_{approximate} = F_{applied} 120 * (1 + \tfrac{1}{2}(0.135)) \quad (8)$$

Alternatively, the actual measurement can be corrected by knowing $F_{reaction}$ 132. In one embodiment, a load sensor is coupled to structure 12 or upper housing 18 to measure when anti-cantilevering structures 64 to measure $F_{reaction}$ 132. $F_{reaction}$ 132 is measured by the load sensor when anti-cantilevering structure 64 couples to upper housing 18. More specifically this will occur when the position of applied load moves into region 82 outside the boundary of triangle 110 of FIG. 5. Measurement system 10 transmits measurement data $F_{reaction}$ 132 and $F_{applied}$ 120 to computer 22 of FIG. 1 to calculate $F_{measured}$ using equation (2) that would be provided on display 24. Since we are measuring $F_{reaction}$ 132 directly we do not need distances $d_1$ and $d_2$ for calculation. In general, each anti-cantilevering structure 62, 64, and 66 will have a force, pressure, or load sensor configured to measure $F_{reaction}$ when anti-cantilevering structure 62, 64, or 66 couples to periphery 38 of upper housing 18.

The second equation (2) supports measurement of $F_{applied}$ 120. The calculation of the second equation requires the distance $d_1$ and $d_2$ to be calculated. The position of the vertexes 72, 74, and 76 are known by computer 22 of FIG. 1. Similarly, the position of anti-cantilevering structures 62, 64, and 66 of FIG. 3 are known by computer 22 of FIG. 1. Distances for $d_1$ and $d_2$ can be calculated by computer 22 using the known positions and measurement data received from measurement system 10 of FIG. 1. Referring to FIG. 8, measurement system 10 would identify that the position of applied load to the actual measured force, pressure, or load ($F_{measured}$) to $F_{reaction}$ and $F_{applied}$.

The second equation is: $F_{applied} 120 = F_{reaction} 132 * d_2/d_1$. The applied force at $F_{applied}$ 120 can be calculated by computer 22 and displayed on display 24 of FIG. 1.

Alternatively, an estimate can be provided by computer 22 and display 24 of FIG. 1. The estimate is provided that provides a simple correction that improves the accuracy of the measurement data within acceptable tolerances required by a surgeon or surgical team reviewing the measurement data as the position of applied load moves outside the boundary of triangle 110 of FIG. 4. Thus, measurements can be provided outside a polygon formed by the sensors located at vertexes of the polygon either by estimate or direct measurement as disclosed herein.

Figure 9:
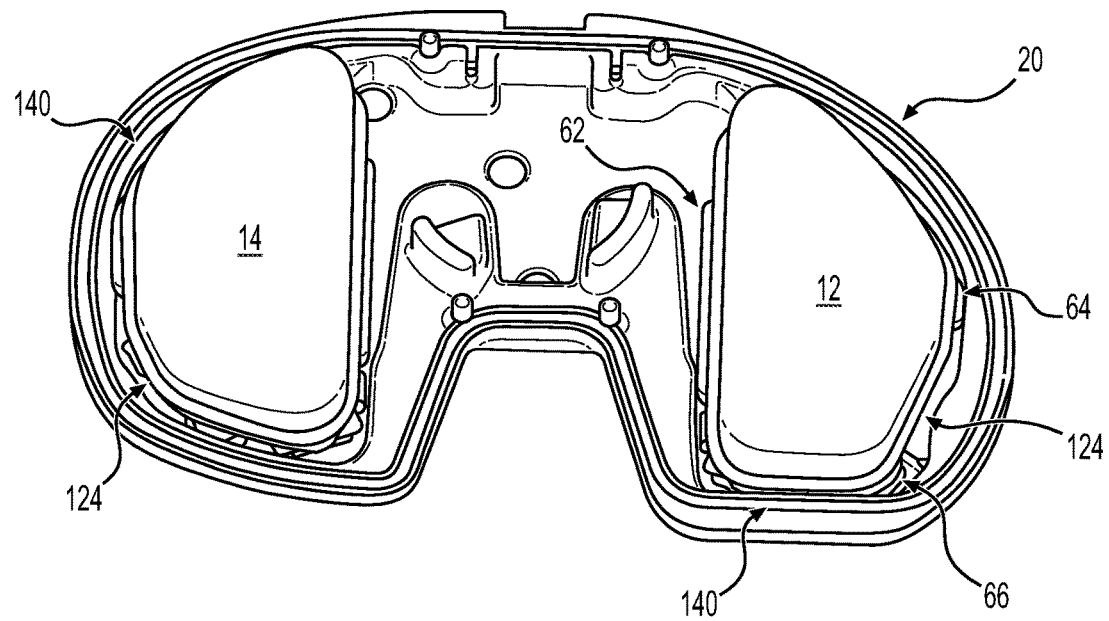
FIG. 9 is an illustration of the bottom housing in accordance with an example embodiment.

FIG. 9 is an illustration of bottom housing 20 in accordance with an example embodiment. Bottom housing 20 is a component of measurement system 10 of FIG. 1. Structure 12 and structure 14 are shown coupled to bottom housing 20. An O-ring 124 is shown coupled around structure 12.

Similarly, an O-ring 124 is shown coupled around structure 14. O-ring 124 is configured to support movement of structure 12 or 14 when a force, pressure, or load is applied to a surface of structure 12 or 14. O-ring 12 is also configured to form a hermetic seal between upper housing 18 (not shown) and structure 12 or 14 to isolate an internal environment of enclosure 16 of FIG. 1 from an external environment. Structure 12 and structure 14 can move independently. Bottom housing 20 has a glue channel 140 that corresponds to a glue channel of upper housing 18 of FIG. 3. In the example, glue channel 140 forms a contiguous channel around the entire periphery of bottom housing 20. Glue channel 140 is configured to hold a glue or adhesive prior to coupling upper housing 18 to bottom housing 20. Glue or adhesive is placed in glue channel 140 around the entirety of glue channel 140 to ensure complete hermetic sealing of enclosure 16 of FIG. 1 when upper housing 18 is mated to bottom housing 20.

Sensors couple to and underlie structure 12 or structure 14 at vertexes of a polygon. Examples of sensors for measuring a force, pressure, or load are mechanical sensors, piezo-sensors, MEMs devices, capacitors, strain gauges, and other pressure sensitive components. The sensors can measure force, pressure, or load directly or indirectly. Computer 22 of FIG. 1 can include calibration data to reduce non-linearities over a range of measurement. In the example, a first sensor, a second sensor, and third sensor underlie and couple to structure 12 respectively at area 52, 54, and 56 of structure 12 of FIG. 3. The first sensor, second sensor, and third sensor measure loading at vertexes 72, 74, and 76 as shown in FIG. 4. Similarly, a fourth sensor, a fifth sensor, and a sixth sensor underlie and couple to structure 12 respectively at area 32, 34, and 36 of FIG. 3. The fourth sensor, fifth sensor, and sixth sensor measure loading respectively at vertex 92, 94, and 96. The position of applied load and the load magnitude applied to structures 12 or 14 can be calculated using measurement data from the first, second, third, fourth, fifth, or sixth sensors. In one embodiment, the measurement data from the sensors is transmitted from enclosure 10 coupled to a musculoskeletal system to computer 22 for calculating the position of applied and the load magnitude.

Figure 10:
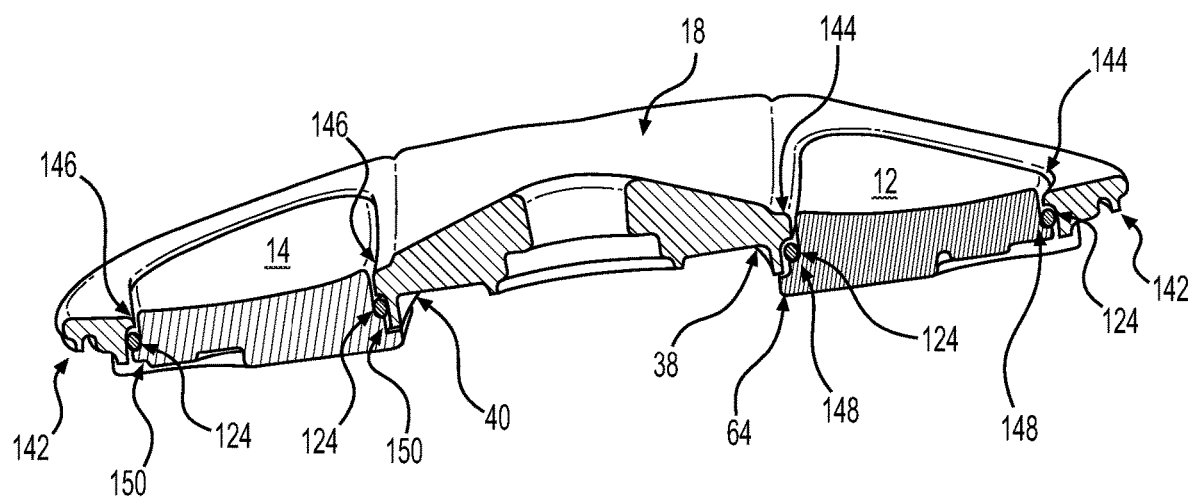
FIG. 10 is a cross-sectional view of the upper housing illustrating the O-ring placed around the structure forming a hermetic seal between the structure and the upper housing in accordance with an example embodiment.

FIG. 10 is a cross-sectional view of upper housing 10 illustrating O-ring 124 placed around structure 12 forming a hermetic seal between structure 12 and upper housing 18 in accordance with an example embodiment. Similarly, O-ring 124 placed around structure 14 forms a hermetic seal between structure 12 and upper housing 18. As stated previously, structure 12 or structure 14 can move relative to the enclosure when a force, pressure, or load is applied to a surface of structure 12 or structure 14. The O-ring 124 coupled to structure 12 is bounded and retained by features on upper housing 18 and structure 12. In one embodiment, a ridge 144 is a feature formed on upper housing 18 on a sidewall of the opening in which structure 12 fits. Similarly, a ridge 148 is formed on structure 12 on a sidewall of structure 12. O-ring 124 couples around structure 12 and is retained by ridge 148. In one embodiment, there is a gap between a sidewall having ridge 144 and structure 12. The gap between the sidewall having ridge 144 is less than the thickness of O-ring 124 to compress O-ring 124 thereby forming a hermetic seal when structure 12 is placed within the opening in upper housing 18. The cross-sectional view shows structure 12 inserted within the opening in upper housing 18. Note that O-ring 124 is bounded by ridge 144 and ridge 148 to retain O-ring 124 compressed between structure 12 and upper housing 18 to maintain the hermetic seal.

Similarly, the O-ring 124 coupled to structure 14 is bounded and retained by features on upper housing 18 and structure 14. In one embodiment, a ridge 146 is a feature formed on upper housing 18 on a sidewall of the opening in which structure 14 fits. A ridge 150 is formed on a sidewall of structure 14 that corresponds to ridge 146. O-ring 124 couples around structure 14 and is retained by ridge 150. In one embodiment, there is a gap between a sidewall having ridge 146 and structure 14. The gap between the sidewall having ridge 146 of is less than the thickness of O-ring 124 to compress O-ring 124 when structure 14 is placed within the opening in upper housing 18. The cross-sectional view shows structure 14 inserted within the opening in upper housing 18. Note that O-ring 124 is bounded by ridge 146 and ridge 150 to retain O-ring 124 compressed between structure 12 and upper housing 18 to maintain the hermetic seal. Alternatively, O-ring 124 can be replaced with a flexible glue or flexible overmold feature that creates a seal/linear bearing effect.

Upper housing 18 couples to bottom housing 20 of FIG. 9. In one embodiment, a glue channel 140 of FIG. 9 is configured to hold glue or an adhesive around the entire perimeter of the bottom housing 20 of FIG. 9. Upper housing 18 has a corresponding glue channel 142. Glue channel 142 is also formed around the entire perimeter of upper housing 18. In one embodiment, glue channel 142 has a ridge configured to fit within glue channel 140 of FIG. 9. The glue or adhesive is placed within glue channel 140 of FIG. 9. Upper housing 18 is coupled to bottom housing 20 of FIG. 9 such that glue channel 140 couples to glue channel 142. In one embodiment, glue channel 142 of upper housing 18 has a feature that extends into glue channel 140 of bottom housing of FIG. 9. The feature of glue channel 142 is configured to couple to the glue or adhesive within and support alignment of upper housing 18 to bottom housing 20 of FIG. 9 to form enclosure 16 of FIG. 1 that is hermetically sealed. Thus, Enclosure 16 of FIG. 1 is hermetically sealed by glue channel 140 of FIG. 9, glue channel 142 of FIG. 10, O-ring 124 on structure 12 and O-ring 124 on structure 14. Electronic circuitry and one or more sensors are housed within enclosure 16 of FIG. 1. In one embodiment, enclosure 16 of FIG. 1 further includes a power source such as a battery or can acquire power or harvest energy from an external source to charge an energy storage device such as a super capacitor to perform a measurement sequence. Measurement data from enclosure 16 is transmitted to computer 22 of FIG. 1 and displayed on display 24. In one embodiment, computer 22 and display 24 of FIG. 1 is configured to provide measurement data related to load magnitude at a position of applied load over the entire surface of structure 12 or structure 14.

In general, FIGS. 1-10 will be referenced herein below to support disclosure of the invention. More specifically, components of FIGS. 1-10 may be called upon to describe aspects of operation or structure herein below. A measurement system 10 is disclosed comprising an enclosure 16 and a computer 22. A measurement device of measurement system 10 comprises enclosure 16, at least one structure (structure 12 or structure 14), electronic circuitry, a power source, and at least one sensor. In general, the measurement device is configured to couple to a musculoskeletal system to generate at least one measurement. In one embodiment, the measurement device is configured to be placed in a joint of the musculoskeletal system. The electronic circuitry, the power source, and the at least one sensor are housed within enclosure 16 and sealed from an external environment. In one embodiment, enclosure 16 comprises an upper housing 16 and a bottom housing 20 coupled together. In one embodiment, the at least one structure is configured to fit within an opening in the enclosure 16. In one embodiment, at least a portion of the surface of the at least one structure is above an adjacent surface of upper housing 16. The surface shape and height of the at least one structure reduces the position of applied load from leaving the at least one structure to the adjacent surface of upper housing 16. In one embodiment, the surface of the at least one structure is non-planar. In one embodiment, the surface of the at least one structure is curved. The surface of the at least one structure is configured to couple to a musculoskeletal system. In the example, structure 12 and structure 14 are configured to fit within openings in enclosure 16 for coupling to a medial condyle and a lateral condyle of a femur. A plurality of sensors underlies and couples to the at least on structure for measuring a force, pressure, or load. Enclosure 16 and the structure are hermetically sealed to isolate an interior of enclosure 16 from an external environment. In one embodiment, an O-ring 124 is placed around the at least one structure (structure 12 or structure 14) such that the O-ring 124 couples between enclosure 16 and the at least one structure to hermetically seal the at least one structure (structure 12 or structure 14) to enclosure 16. The O-ring also supports movement of structure 12 or structure 14 relative to enclosure 16 when a force, pressure, or load is applied to the surface of structure 12 or structure 14. O-ring 124 is retained by two or more features configured to confine O-ring 124 within a predetermined area. In the example, a ridge 144 is formed in upper housing 18 and a ridge 148 is formed in structure 12 as retaining features for O-ring 124. O-ring 124 is compressed between sidewalls of upper housing 18 and structure 12. Ridge 144 and ridge 148 retains O-ring 124 from moving up or down thereby maintaining a seal over the range of motion of structure 12 under a force, pressure, or load. In one embodiment, the plurality of sensors couple to the surface of the at least one structure at vertexes of a polygon. In one embodiment, the at least one structure includes at least three anti-cantilevering structures where at least one of the anti-cantilevering structures is configured to couple to the enclosure to limit canting of the at least one structure when the musculoskeletal system couples to the surface of the at least one structure outside a predetermined area. The measurement device of measurement system 10 transmits measurement data to computer 22. Computer 22 calculates a position of applied load by the musculoskeletal system to the surface of the at least one structure of the measurement device and a load magnitude at the position of applied load from the sensor data from the measurement device. In one embodiment, computer 22 is configured to estimate the load magnitude at the position of applied load (by the musculoskeletal system) when at least one anti-cantilevering structure in enclosure 16 prevents canting of structure 12 or structure 14. In one embodiment, anti-cantilevering structures are formed on structure 12 and structure 14 that couple to upper housing 18 to limit canting. Alternatively, anti-cantilevering structures can be formed on upper housing 18 or bottom housing 20. In the example, anti-cantilevering structures 62, 64, or 66 are formed on structure 12 of enclosure 16 and anti-cantilevering structures 42, 44, or 46 are formed on structure 14 of enclosure 16. Anti-cantilevering structure 62, 64, or 66 limit canting when a force pressure, or load is applied to the surface structure 12 in region 78, 80, or 82. Similarly, Anti-cantilevering structure 42, 44, or 46 limit canting when a force, pressure, or load is applied to the surface of structure 14 in region 98, 100, or 102.

The measurement device is configured to be placed the musculoskeletal system such as in bone, a spine, a knee, a hip, a shoulder, an ankle, fingers, wrist, elbow, or toes. In the example, the measurement device is configured to be placed in a knee joint of the musculoskeletal system. Measurement system 10 is configured to measure a force, pressure, or load applied by a medial condyle and lateral condyle of a femur. In one embodiment, the surface of the at least one structure (structure 12 or structure 14) couples within the joint and supports movement of the joint. In one embodiment, the measurement device includes at least three sensors are configured to measure a force, pressure, or load applied to the surface of the at least one structure. The electronic circuitry couples to the at least three sensors and is configured to control a measurement process and transmit measurement data. The at least one structure (structure 12 or structure 14) is configured to move under loading to apply the force, pressure, or load to the at least three sensors. Computer 22 is configured to receive the measurement data from the measurement device. Computer 22 is configured to calculate a position of applied load on the surface of the structure (structure 12 or structure 14) and a load magnitude at the position of applied load. In one embodiment the predetermined area of the surface of the structure (structure 12 or structure 14) is the polygon defined by the at least three sensors that couple to the surface at vertexes of the polygon. In the example, the three sensors couple to the surface of the structure (structure 12 or structure 14) at vertexes of a triangle.

At least three regions exist outside the boundary of the polygon on the surface of the structure (structure 12 or structure 14) defined by the at least three sensors underlying the surface that measure the force, pressure, or load applied to the surface. As previously mentioned, the at least three sensors are placed at vertexes of the polygon that can be related to the surface of the structure (structure 12 or structure 14) as seen in FIG. 4. In the example, a region 78, a region 80, and a region 82 are outside the predetermined area of the surface of structure 12. In the example, the predetermined area is triangle 110 having vertexes 72, 74, and 76 shown on the surface of structure 12. Computer 22 is configured to correct the load magnitude when the position of applied load is in region 78, region 80, or region 82. In the example, computer 22 applies a first correction, a second correction or a third correction when the position of applied load is respectively in region 78, region 80, and region 82 to reduce measurement error. In the example, the first correction, the second correction, or the third correction is a constant. Alternatively, the first correction, the second correction, or the third correction can be more complex to further reduce the error.

One or more stop features are formed within enclosure 16. A stop feature is configured to limit movement of structure 12 or structure 14. In one embodiment, the stop feature prevents movement of structure 12 or structure 14 beyond a predetermined distance. In one embodiment, the stop feature prevents a force, pressure, or load from being applied to a surface of structure 12 or structure 14 that can damage the one or more sensors configured for measuring the force, pressure, or load applied to structure 12 or structure 14. In the example, a stop 126 is formed in bottom housing 20 underlying structure 12 or structure 14. In the example, stop 126 is configured to support compression of sensor 122 but prevents compression of sensor 122 beyond a predetermined distance. The predetermined distance between structure 12 and stop 126 is a function of the range of measurement by measurement system 10 and the limit of reliable sensing by sensor 122. In general, the predetermined distance between structure 12 and stop 126 is selected to keep sensor 122 within a range of operation that is specified by the sensor manufacturer for sustainable and reliable performance. In one embodiment, stops can be formed in more than one location underlying structure 12 or structure 14. In one embodiment, the predetermined distance between the stop and structure 12 supports a maximum measurement but can prevent measurement by sensor 122 above the maximum measurement as stop 126 prevents further movement of structure 12 and thereby further loading applied to sensor 122.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does not yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact measurement device or surgical apparatus may be applicable to many medical applications monitoring or measuring physiological parameters throughout the human body including, not limited to, bone density, movement, position, orientation, force, pressure, load, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims. While the subject matter of the invention is described with specific examples of embodiments, the foregoing drawings and descriptions thereof depict only typical embodiments of the subject matter and are not therefore to be considered to be limiting of its scope, it is evident that many alternatives and variations will be apparent to those skilled in the art. Thus, the description of the invention is merely descriptive in nature and, thus, variations that do not depart from the gist of the invention are intended to be within the scope of the embodiments of the present invention. Such variations are not to be regarded as a departure from the spirit and scope of the present invention.

While the present invention has been described with reference to embodiments, it is to be understood that the invention is not limited to the disclosed embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of an invention. Furthermore, while some embodiments described herein include some but not other features included in other embodiments, combinations of features of different embodiments are meant to be within the scope of the invention, and form different embodiments, as would be understood by those skilled in the art.

What is claimed is:

1. A measurement device to measure loading applied by a musculoskeletal system comprising:
   an enclosure comprising an upper housing and a lower housing;
   a structure having a surface to couple to the musculoskeletal system, wherein the structure fits within an opening of the enclosure, wherein a plurality of sensors are coupled to a surface of the structure, wherein the structure includes an anti-cantilevering structure, wherein the anti-cantilevering structure couples to the enclosure to limit canting of the structure when the musculoskeletal system contacts the surface of the structure outside a predetermined area, wherein the anti-cantilevering structure overhangs a periphery of the upper housing, wherein a first region, a second region, and a third region of the surface of the structure are outside the predetermined area, wherein the anti-cantilevering structure is a first anti-cantilevering structure, wherein the measurement device further includes a second anti-cantilevering structure and a third anti-cantilevering structure, wherein the first anti-cantilevering structure, the second anti-cantilevering structure, or the third anti-cantilevering structure are configured to limit canting of the structure when a position of an applied load is in the first region, the second region, or the third region.

2. The measurement device of claim 1, wherein the measurement device is configured to be placed within a joint of the musculoskeletal system, and wherein the surface of the structure is configured to support movement of the joint.

3. The measurement device of claim 1, further including:
   electronic circuitry coupled to the plurality of sensors, wherein the electronic circuitry is configured to control a measurement process and transmit measurement data; and
   a computer configured to receive the measurement data, wherein the computer is configured to calculate a position of an applied load on the surface of the structure and a load magnitude at the position of the applied load.

4. The measurement device of claim 3, wherein the computer is configured to correct the load magnitude when the position of the applied load is in the first region, the second region, or the third region.

5. The measurement device of claim 4, wherein the computer applies a first correction, a second correction, or a third correction to the load magnitude when the position of the applied load is respectively in the first region, the second region, or the third region to reduce measurement error.

6. The measurement device of claim 1, wherein the plurality of sensors couple to the surface of the structure at vertexes of a polygon, and wherein the predetermined area is the polygon.

7. The measurement device of claim 1, wherein the upper housing has the opening of the enclosure, and wherein an O-ring couples between the structure and the upper housing to support movement of the structure relative to the enclosure.

8. The measurement device of claim 7, wherein the O-ring is coupled between a retaining feature of the upper housing and a retaining feature of the structure.

9. The measurement device of claim 1, wherein a portion of the surface of the structure is above an adjacent surface of the enclosure.

10. The measurement device of claim 1, wherein the surface of the structure is curved.

11. The measurement device of claim 1, wherein the anti-cantilevering structure is positioned a predetermined distance from the periphery of the upper housing.

12. The measurement device of claim 1, wherein an overhang distance of the anti-cantilevering structure relative to the periphery of the upper housing varies based on the applied load, wherein the overhang distance of the anti-cantilevering structure is a distance the anti-cantilevering structure overhangs the periphery of the upper housing.

13. A measurement device configured to measure loading applied by a musculoskeletal system, the measurement device comprising:
   an enclosure;
   a structure configured to move relative to the enclosure, wherein the structure has a surface configured to couple to the musculoskeletal system and wherein the surface of the structure couples to a plurality of load sensors, wherein each of the plurality of load sensors define a vertex of a predetermined area of the surface;
   electronic circuitry within the enclosure, wherein the electronic circuitry is coupled to the plurality of load sensors, wherein the electronic circuitry is configured to control a measurement process and transmit measurement data; and
   a computer configured to receive the measurement data, wherein the surface of the structure is configured to couple to the musculoskeletal system, wherein the computer is configured to calculate (i) a position of an applied load to the surface of the structure and (ii) a load magnitude at the position of the applied load, wherein the computer is configured to determine when the position of the applied load is outside the predetermined area of the surface, and wherein the computer corrects the load magnitude at the position of the applied load when the position of the applied load is outside the predetermined area of the surface, wherein the enclosure includes a plurality of anti-cantilevering structures, wherein the plurality of anti-cantilevering structures are configured to limit canting of the structure when the position of the applied load is outside the predetermined area of the surface, and wherein the enclosure includes at least one stop feature.

14. The measurement device of claim 13, wherein the measurement device is configured to be placed within a joint of the musculoskeletal system, wherein the surface of the structure is configured to support movement of the joint, wherein the computer is configured to utilize a constant to correct the load magnitude, and wherein the constant is used by the computer to adjust the load magnitude when the position of the applied load is outside the predetermined area of the surface.

15. The measurement device of claim 13, wherein the enclosure has an opening, wherein an O-ring couples between the structure and an upper housing to support movement of the structure within the opening, and wherein the O-ring is coupled between a retaining feature of the enclosure.

16. The measurement device of claim 13, wherein a portion of the surface of the structure is above an adjacent surface of the enclosure.

17. A measurement device configured to measure loading applied by a musculoskeletal system, the measurement device comprising:
   an upper housing;
   a lower housing, wherein the upper housing and the lower housing are configured to couple together to form an enclosure to house electronic circuitry and a plurality of load sensors; and
   a structure having a surface configured to couple to a joint of the musculoskeletal system, wherein the structure is configured to fit within an opening in the upper housing, wherein the structure couples to the plurality of load sensors, wherein an O-ring couples between the upper housing and the structure, wherein the upper housing and the structure each include at least one retaining feature to retain the O-ring between the upper housing and the structure, wherein the surface of the structure is configured to couple to the musculoskeletal system, wherein the structure is configured to move relative to the enclosure, wherein the surface of the structure is above an adjacent surface of the upper housing, and wherein the enclosure includes one or more anti-cantilevering structures to prevent canting that can unload at least one of the plurality of load sensors.

18. The measurement device of claim 17 further including:
   the electronic circuitry within the enclosure coupled to the plurality of load sensors, wherein the electronic circuitry is configured to control a measurement process and transmit measurement data; and
   a computer configured to receive the measurement data, wherein the computer is configured to calculate a position of an applied load to the surface of the structure and a load magnitude at the position of the applied load, wherein the computer is configured to determine when the position of the applied load is outside a predetermined area of the surface, and wherein the computer corrects the load magnitude at the position of the applied load when the position of the applied load is outside the predetermined area.

* * * * *